US010881273B2

(12) United States Patent
Backman et al.

(10) Patent No.: US 10,881,273 B2
(45) Date of Patent: Jan. 5, 2021

(54) PRE-FABRICATED, ON-DEMAND INTERFACE FOR USE IN PROVIDING OPTICAL COUPLING BETWEEN DISPOSABLE AND REUSABLE MEMBERS OF A LOW COHERENCE ENHANCED BACKSCATTERING FIBER-OPTIC PROBE

(71) Applicants: NORTHWESTERN UNIVERSITY, Evanston, IL (US); AMERICAN BIOOPTICS LLC, Evanston, IL (US)

(72) Inventors: Vadim Backman, Chicago, IL (US); Bradley Gould, Evanston, IL (US); Andrew J. Cittadine, Chicago, IL (US); Nikhil Mutyal, Maharashtra (IN)

(73) Assignees: Northwestern University, Evanston, IL (US); American Biooptics LLC, Evanston, IL (US)

( * ) Notice: Subject to any disclaimer, the term of this patent is extended or adjusted under 35 U.S.C. 154(b) by 840 days.

(21) Appl. No.: 14/638,714

(22) Filed: Mar. 4, 2015

(65) Prior Publication Data
US 2016/0256037 A1   Sep. 8, 2016

(51) Int. Cl.
*A61B 1/00*   (2006.01)
*A61B 5/00*   (2006.01)
(Continued)

(52) U.S. Cl.
CPC ...... *A61B 1/00126* (2013.01); *A61B 1/00103* (2013.01); *A61B 5/0084* (2013.01);
(Continued)

(58) Field of Classification Search
CPC .......... A61B 2090/306; A61B 1/00103; A61B 1/00126
See application file for complete search history.

(56) References Cited

U.S. PATENT DOCUMENTS

| 5,199,431 A | * | 4/1993 | Kittrell | .............. | A61B 1/00096 |
| | | | | | 600/476 |
| 2006/0184162 A1 | * | 8/2006 | Smith | ..................... | A61F 9/007 |
| | | | | | 606/4 |

(Continued)

FOREIGN PATENT DOCUMENTS

WO   97/19375 A1   5/1997

OTHER PUBLICATIONS

Sep. 14, 2017 International Preliminary Report on Patentability issued in International Application No. PCT/US2016/019864.
(Continued)

*Primary Examiner* — Serkan Akar
(74) *Attorney, Agent, or Firm* — Leydig, Voit & Mayer, Ltd.

(57) ABSTRACT

A pre-fabricated, on-demand interface provides optical coupling between disposable and reusable portions of a fiber-optic probe. The interface uses a pre-cured, compressible optically-transmissive gel in a cavity of the disposable portion, which can be a disposable insertion tip of the fiber optic probe. The disposable portion includes an elongated housing, or sheath, and the cavity is located within and proximal of a distal end of the elongated housing. A proximal end of an optical assembly of the disposable portion is located within the cavity and contacts the gel. A first coupling, provided at a proximal end of the elongated housing, detachably couples to a mating, second coupling of the probe reusable portion. When the disposable and reusable portions are coupled together, the gel is compressed between the proximal end of the optical assembly of the disposable portion and a distal optical member of an optical assembly of the reusable portion.

17 Claims, 7 Drawing Sheets

(51) Int. Cl.
G02B 6/36 (2006.01)
G02B 6/24 (2006.01)
G02B 6/38 (2006.01)
A61B 90/30 (2016.01)

(52) U.S. Cl.
CPC ............ *G02B 6/24* (2013.01); *G02B 6/3624* (2013.01); *G02B 6/382* (2013.01); *G02B 6/387* (2013.01); *A61B 2090/306* (2016.02); *A61B 2560/0285* (2013.01); *A61B 2562/146* (2013.01)

(56) References Cited

U.S. PATENT DOCUMENTS

| | | |
|---|---|---|
| 2007/0129615 A1 | 6/2007 | Backman et al. |
| 2010/0262020 A1 | 10/2010 | Backman et al. |
| 2012/0209074 A1 | 8/2012 | Titus |
| 2012/0289858 A1* | 11/2012 | Ouyang ............. A61B 10/0275 600/562 |
| 2014/0036271 A1* | 2/2014 | Backman ............. G01N 21/474 356/446 |
| 2014/0275765 A1 | 9/2014 | Gebhart et al. |
| 2016/0081712 A1* | 3/2016 | Heniford .............. A61B 5/0066 600/424 |

OTHER PUBLICATIONS

May 6, 2016 International Search Report and Written Opinion in PCT/US2016/019864.

* cited by examiner

PRE-FABRICATED, ON-DEMAND INTERFACE FOR USE IN PROVIDING OPTICAL COUPLING BETWEEN DISPOSABLE AND REUSABLE MEMBERS OF A LOW COHERENCE ENHANCED BACKSCATTERING FIBER-OPTIC PROBE

This invention was made with government support under grant no. R01 CA128641 awarded by the National Institutes of Health. The government has certain rights in the invention.

This application is related to U.S. patent application Ser. No. 11/604,659 (published as U.S. Patent Application Publication No. 2007/0129615), U.S. patent application Ser. No. 12/684,837 (published as U.S. Patent Application Publication No. 2010/0262020) and U.S. patent application Ser. No. 13/963,560 (published as U.S. Patent Application Publication No. 2014/0036271), the disclosures of which are incorporated herein by reference in their entireties.

BACKGROUND

An exemplary implementation of the inventive principles described herein relates to probe apparatus and component combinations that are used to possibly detect abnormal living tissue by detecting an early increase in microvascular blood supply and to detect tissue in close proximity to the abnormal living tissue.

A technique has been developed to acquire optical properties from tissue of a patient to potentially be used in risk-stratification or pre-screening of various types of cancers. This technique uses a small diameter, minimally-invasive probe containing various optical elements. In order to prevent cross-contamination between patients within this setting, either (i) a portion of, or (ii) the entire device must be made disposable. As a completely disposable version of this device is not deemed financially viable, a partially disposable version, in which the patient-inserted portion is disposed of, is preferable. In addition, improved methods for creating an optical coupling between the disposable and reusable portions of this device are desirable.

SUMMARY

In other fiber-optic applications such as telecommunications, on-demand fiber interconnects and splices are generally created by applying an uncured, index-matched optical gel between two mating components. Cured optical gels have also been used historically for providing optical coupling of fibers in re-matable connectors. However, such approaches are not feasible in a disposable probe application for at least two reasons. First, inconsistencies at the optical interface and subsequent undesired internal reflections within the optical path of the coupled device are induced as a result of either a) human error in the method and amount of gel application, or b) the non-viscous nature of the uncured gel itself. The variable reflections associated with the use of an uncured optical gel would be too variable to provide a consistent level and shape of spectrum for effective normalization. Second, gel application is undesirable at the primary-care and OBGYN setting from the standpoint of 1) the difficulty of the application process for a physician, and 2) the potential for human error by the physician, such as forgetting to apply the gel or not applying a sufficient amount of gel.

Exemplary implementations of the inventive principles described herein set forth improvements and solutions with relation to the above challenges.

According to one aspect of the invention, a pre-fabricated, on-demand interface provides optical coupling between disposable and reusable portions of a fiber-optic probe. The interface uses a pre-cured, compressible optically-transmissive gel in a cavity of the disposable portion, such as a disposable insertion tip of a fiber optic probe. A connector is provided at a proximal end of an elongated housing (or sheath) of the disposable portion. The connector includes a first coupling that detachably couples to a mating, second coupling of the reusable portion of the fiber optic probe. The cavity containing the pre-cured, compressible optically-transmissive gel is provided within and near (just proximal of) a distal end of the elongated housing (or sheath), which is the location of the optical interface between the reusable and disposable portions. An optical assembly of the disposable portion is provided at the distal end of the elongated housing (sheath). The pre-cured, compressible optically-transmissive gel disposed inside the cavity contacts at least a proximal end of the optical assembly. When the disposable and reusable portions are engaged with each other, the gel is compressed against surfaces of optical assemblies of the disposable and reusable portions.

One aspect of the invention relates to a disposable insertion tip of a fiber optic probe. The disposable insertion tip is a hygienic disposable sheath. The insertion tip includes an elongated housing having a distal end and a proximal end, the distal end being insertable into a human cavity. An optical assembly is provided at the distal end of the elongated housing and has a proximal end that extends into a cavity provided near the distal end of the elongated housing. In addition, a connector is disposed at a proximal end of the elongated housing. The connector includes a first coupling that detachably couples to a mating, second coupling of a reusable portion of the fiber optic probe. A pre-cured, compressible optically-transmissive gel is disposed inside the cavity and contacts at least the proximal end of the optical assembly.

Preferably, the gel is index-matched to the optical material of the optical assembly.

According to some embodiments, the cavity includes a recess that surrounds at least part of a circumference of the proximal end of the optical assembly, and the gel flows into the recess upon compression of the gel when the connector of the disposable insertion tip is coupled to the reusable portion of the fiber optic probe. In particular, when the disposable insertion tip is connected to the reusable portion of the fiber optic probe, a distal end of an optical assembly of the reusable portion contacts the gel, and the gel is then compressed between the distal end of the optical assembly of the reusable portion and the proximal end of the optical assembly of the disposable insertion tip.

According to some embodiments, the optical assembly of the disposable insertion tip is glass or plastic.

Preferably, the gel has a hardness of between about 60 shore 00 durometer and about 80 shore 00 durometer. According to some embodiments, the gel has a hardness of about 77 shore 00 durometer.

According to another aspect of the invention, a fiber optic probe includes (1) the disposable insertion tip described above, and (2) a reusable portion having (i) a connector disposed proximally of a distal end of the reusable portion, the connector having the mating, second coupling that detachably couples to the first coupling of the disposable insertion tip, and (ii) an optical assembly including a distal optical member disposed at a distal end of the reusable portion and which is located distally of the second coupling. When the first and second couplings are engaged with each other, the pre-cured, compressible optically-transmissive gel is compressed against and contacts at least a distal surface of the distal optical member.

In the fiber optic probe, the gel preferably is index-matched to the optical assembly of the disposable insertion tip and to the distal optical member of the reusable portion.

In the fiber optic probe, the cavity of the disposable insertion tip can include a recess that surrounds at least part of a circumference of the distal optical member, and the gel flows into the recess upon compression of the gel when the first and second couplings are engaged with each other.

In the fiber optic probe, the first and second couplings are positioned on the disposable and reusable portions, respectively, such that the gel undergoes compression without undergoing plastic deformation when the first and second couplings are engaged with each other.

In the fiber optic probe, the distal optical member can be glass or plastic.

BRIEF DESCRIPTION OF THE DRAWINGS

These and other aspects and features of the invention will become apparent to those of ordinary skill in the art upon review of the following description in conjunction with the accompanying figures.

DETAILED DESCRIPTION OF EMBODIMENTS

Exemplary implementations of the inventive principles described herein are intended as illustrative only since numerous modifications and variations will be apparent to those skilled in the art. Various implementations are now described in detail in relation to the drawings.

An exemplary implementation relates to a probe apparatus that is used for optically examining a target for tumors or lesions using what is referred to as "Early Increase in microvascular Blood Supply" (EIBS) that exists in tissues that are close to, but not themselves, the lesion nor tumor. Exemplary implementations also relate to probe apparatus that are used to screen for possibly abnormal tissue using Low-coherence Enhanced Backscattering (LEBS) spectroscopy. While the abnormal tissue can be a lesion or tumor, the abnormal tissue can also be tissue that precedes formation of a lesion or tumor, such as precancerous adenoma, aberrant crypt foci, tissues that precede the development of dysplastic lesions that themselves do not yet exhibit dysplastic phenotype, and tissues in the vicinity of these lesions or pre-dysplatic tissues.

In one exemplary implementation, an application is for detection of such lesions in colonic mucosa in early colorectal cancer, but other applications are described as well.

Figure 1A:
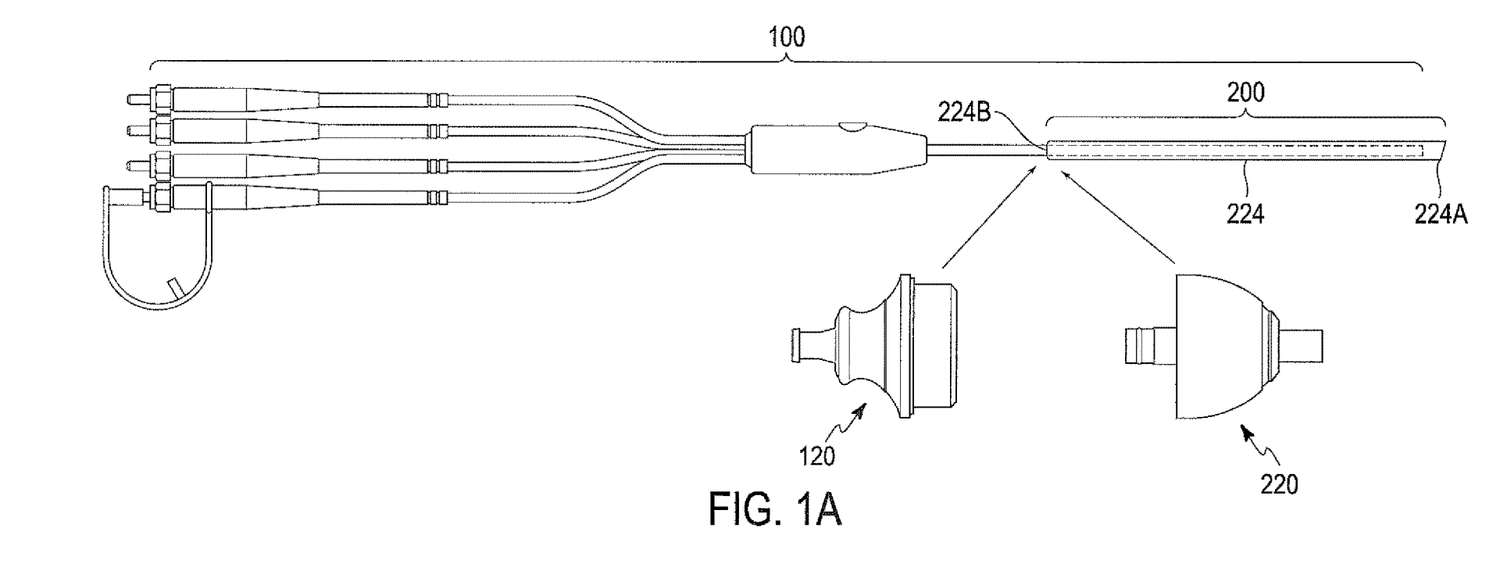
FIG. 1A shows a fiber optic probe having a reusable (trunk) portion and a disposable (insertion tip) portion according to an embodiment of the invention.
Figure 1B:
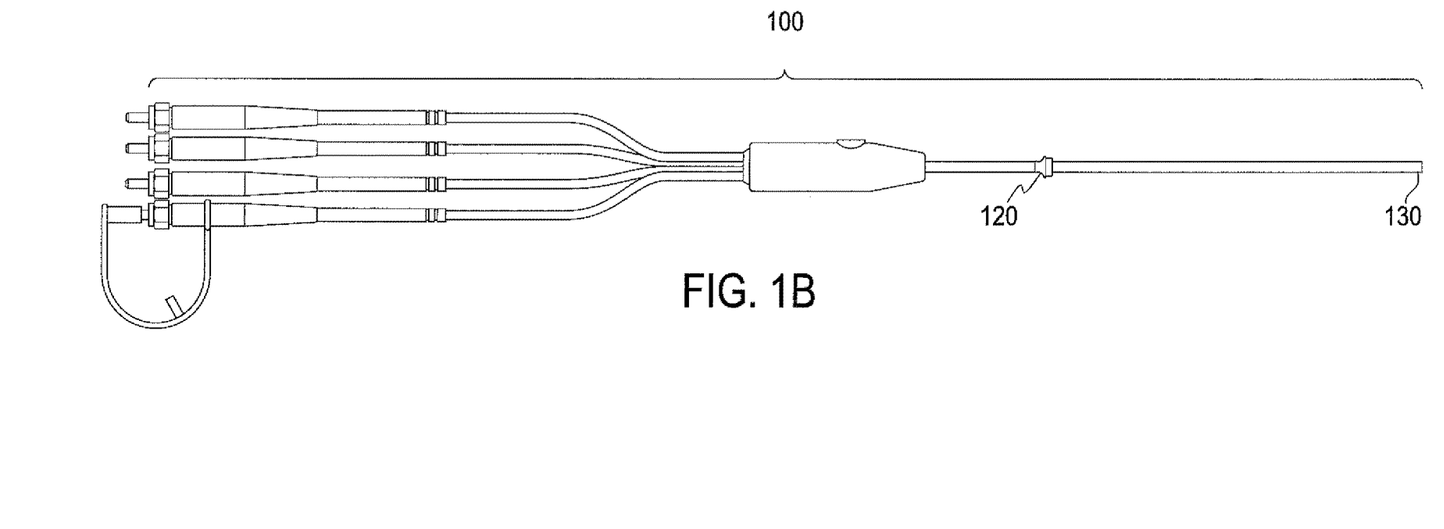
FIG. 1B shows only the reusable (trunk) portion of the fiber optic probe according to the FIG. 1A embodiment.
Figure 1C:
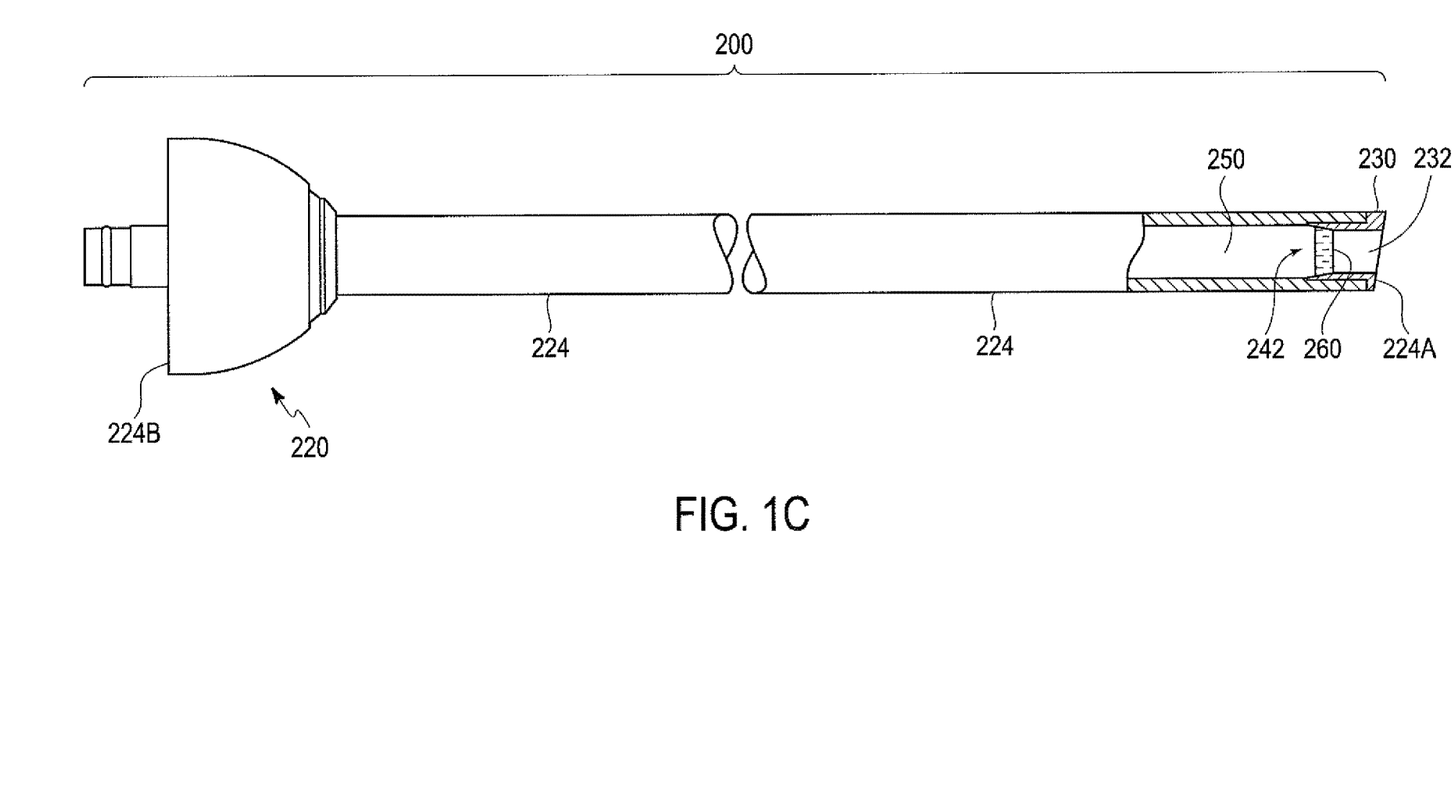
FIG. 1C shows only the disposable (insertion tip) portion of the fiber optic probe according to the FIG. 1A embodiment.

As can be seen from FIGS. 1A-IC, a reusable portion (trunk) 100 is capable of interfacing with a disposable portion (insertion tip) 200. Specifically, a distal portion of the reusable portion (trunk) 100 can be inserted into the disposable portion 200, which is a disposable hygienic sheath that covers the distal portion of the reusable portion 100. (Herein "distal" refers to the end closest to the human subject, whereas "proximal" refers to the end farthest from the human subject.) The optical assemblies of the reusable portion 100 and the disposable portion 200 are capable of transmitting light from a light source, such as a xenon lamp or a light emitting diode. The reusable portion of the probe can comprise illumination fibers that are optically coupled to the light source. For more details on the optical assembly, see, for example, the above-mentioned U.S. patent application Ser. No. 11/604,659 (published as U.S. Patent Application Publication No. 2007/0129615), U.S. patent application Ser. No. 12/684,837 (published as U.S. Patent Application Publication No. 2010/0262020) and U.S. patent application Ser. No. 13/963,560 (published as U.S. Patent Application Publication No. 2014/0036271), the disclosures of which are incorporated herein by reference in their entireties. The remainder of the present description focuses mainly on the disposable portion 200 and the optical interface, and physical connection, between the reusable and disposable portions.

Because a significant length of the probe (e.g., 10-30 cm) is to be inserted into a cavity, for example, colon, of a human subject (patient), the disposable portion 200 must have a length that is greater than the length to be inserted into the body (i.e., the disposable portion should have a length greater than about 10-30 cm). In addition, an optical path extends to the distal tip of the probe because the distal tip is pressed against the tissue that is to be optically sampled. If the (e.g., 10-30 cm) distal portion of the probe that is to be inserted into the patient is made to be entirely disposable, the cost of the disposable portion may be too high because a lengthy optical portion will make up the disposable portion.

According to the embodiments described herein, the disposable portion 200 is an elongated hollow housing (i.e., a sheath) that can be placed over the distal portion of the reusable portion. The distal end of the disposable portion (i.e., the distal end of the elongated housing) includes an optical assembly that extends into a cavity formed inside the elongated housing. A proximal end of the optical assembly of the disposable portion interfaces with a distal optical member of the optical assembly of the reusable portion inside the elongated housing. The proximal end of the elongated housing of the disposable portion includes a connector having a first coupling that detachably engages with a second coupling provided on the reusable portion proximally spaced from the distal end of the reusable portion. The connector thus will be disposed outside of the patient while the distal end of the probe is inserted into the patient, and thus the portions of the probe that are inserted into the patient can be kept relatively smaller in diameter, even if the connector is relatively large. Moreover, even though a substantial length (e.g., 10-30 cm) of the reusable portion is inserted into the patient, the inserted portion is covered by the disposable portion, and thus can be reused. Furthermore, the disposable portion has an optical assembly only at its distal end. The optical assembly of the disposable portion is comprised only of the glass or plastic optical member at the tip and the gel, and thus the cost of the disposable portion can be kept low compared to the more complex optical assembly of the probe, which includes a glass or plastic tip, optical fibers, fiber alignment ferrules and connectors, etc.

Referring to FIGS. 1A-1C, a disposable insertion tip 200 of the fiber optic probe includes an elongated hollow housing 224 having a distal end 224A and a proximal end 224B. The distal end 224A is insertable into a human cavity to be inspected. An optical assembly 230 is provided at the distal end 224A of the elongated housing 224. The optical assembly 230 includes an optical member 232 having distal and proximal ends. The distal end of the optical member 232 will contact the tissue to be inspected when the probe is inserted into the patient, whereas the proximal end of the optical member 232 contacts a pre-cured gel 260 (to be described later) that is provided in a cavity 242 within the distal end of the elongated housing 224. The optical member 232 can be glass, but other materials are possible such as, for example, optical grade polymers such as acrylic, for example.

A connector 220 is disposed at the proximal end 224B of the elongated housing 224. The connector 220 includes a first coupling that detachably couples to a mating, second coupling provided on a connector 120 of the reusable portion 100 of the fiber optic probe.

As noted above, the proximal end of the optical member 232 is located in the cavity 242 which is within the distal end of the elongated housing 242. A pre-cured, compressible optically-transmissive gel 260 is disposed inside the cavity 242 and contacts at least the proximal-most surface of the optical member 232.

The connector 120 of the reusable portion 100 is disposed proximally of the distal end of the reusable portion 100. A distal optical member 130 of an optical assembly of the reusable portion 100 is provided at the distal end of the reusable portion 100. When assembled, the distal portion of the reusable portion 100 is inserted through a passage 250 extending longitudinally through the disposable portion 100, and then the connectors 120 and 220 are engaged with each other.

When the reusable portion 100 is coupled to the disposable portion 200, the gel 260 functions as an interface between the distal optical member 130 of the reusable portion 100 and the proximal end of the optical member 232 of the disposable portion 200. The pre-cured gel 260 may be index-matched to the distal optical member 130 and to the optical member 232 and can further provide for minimal absorption of inputted optical light. In one implementation, the gel 260 can provide minimal absorption of inputted optical light (e.g., <<1% in the applicable wavelength range). The cured gel 260 can have optical index values of 1.5463, 1.0587 and 1.5074 at 402 nm, 589.3 nm and 632.8 nm, respectively. An implementation can employ NyoGel® OCK-425 optical curing gel and NyoGel® OCK-425 optical curing gel with the addition of an adhesion promoter to assist in gel adhesion to the optical element in the disposable portion 200. Another implementation can employ NyoGel® OCK-451 optical curing gel and NyoGel® OCK-451 optical curing gel with the addition of an adhesion promoter to assist in gel adhesion to the optical element in the disposable portion 200.

The gel is fluid in its uncured state, but after curing, for example, by application of heat or UV irradiation, the gel remains in place (i.e., the gel does not flow) but is compressible. The uncured gel would be placed into the cavity 242 of the disposable portion 200 and in contact with the optical member 232 during manufacture of the disposable portion, and then cured, for example, by application of heat. The disposable portion 200 then would be placed in a sealed package so as to remain hygienic or sterile until use. By "pre-cured", it is meant that the user receives the hygienic or sterile, packaged, disposable portion 200 with the gel already cured. So, "pre-cured" means that the gel has been cured before the disposable portion 200 is provided to the end user.

The gel (or gel layer) 260 is capable of compressing and can also be sufficiently flexible as to provide for adequate conformability to the distal optical member 130 and the proximal end of the optical member 232. The gel may be made of varying degrees of hardness or durometer with differing results. In one implementation, the durometer of the gel may be between about 60 shore 00 to about 80 shore 00. In another implementation, the durometer of the gel may be 77 shore 00. The gel's conformability allows for the normal handling of the fiber optic probe (such as flexing and vibration) that induces movement or shifting between the reusable and disposable portions 100 and 200 to inhibit the ingress of air between the optical members 130 and 232. The ingress of air results in substantial amounts of undesired internal specular reflections within the optical path of the device due to differences in index of refraction between the reusable optical member 130 and subsequent air gaps between the disposable optical member 232 and the gel layer 260. In one implementation, the pre-cured gel layer 260 in the uncompressed state can be 1.5 mm thick (dimension D1 in FIG. 2A).

In a fully coupled state, the proximal end of the optical member 232 makes contact with the gel layer 260 within the cavity 242 of the disposable portion 200, the distal end of the distal optical member 130 makes contact with the gel layer 260 within the cavity 242 of the disposable portion 200, and both axial and rotational positions of the distal optical member 130 and the optical member 232 are fixed relative to one another via the engagement of the connectors 120 and 220.

Figure 2A:
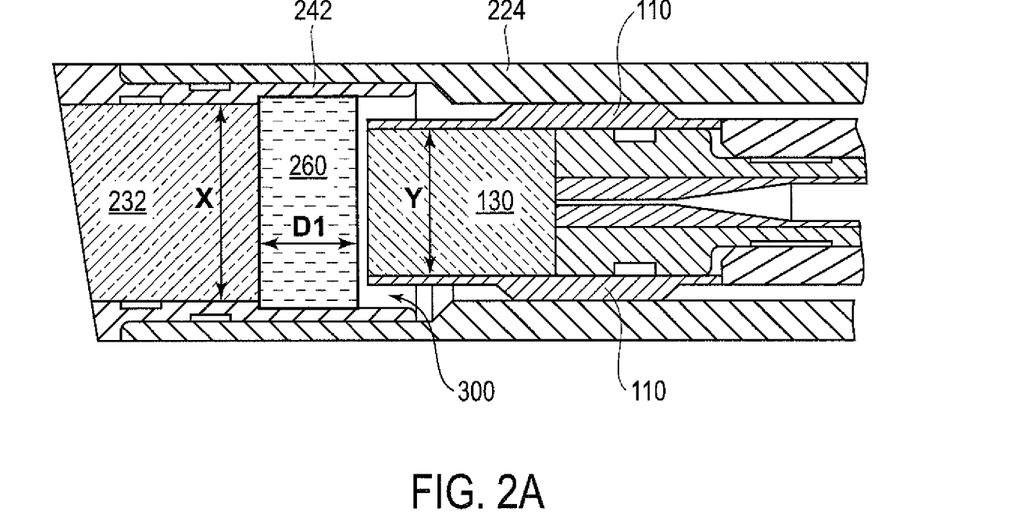
FIG. 2A shows a detailed partially cross-section view of the optical interface between the reusable portion and the disposable portion with the gel in an uncompressed state and showing a recess provided in a cavity of the disposable portion.
Figure 2B:
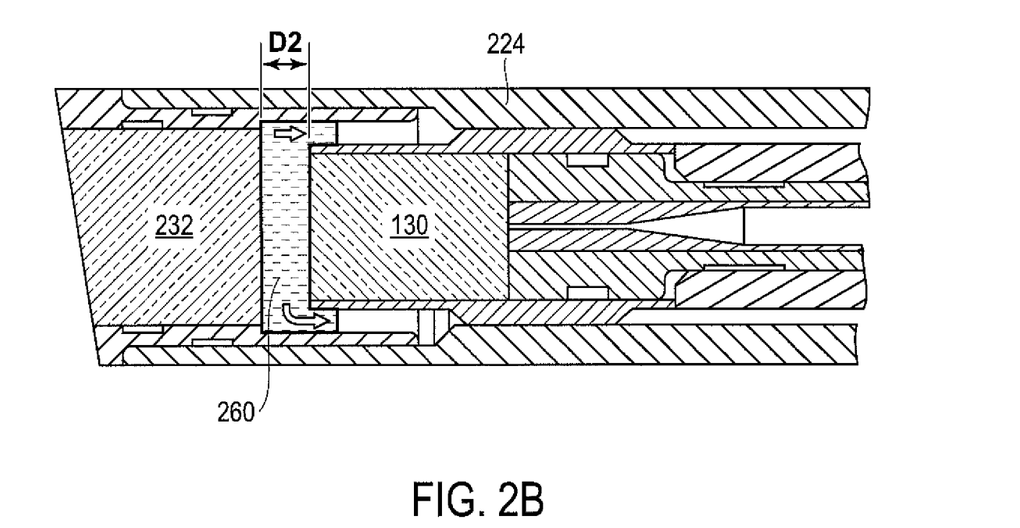
FIG. 2B shows a detailed partially cross-section view of the optical interface between the reusable portion and the disposable portion with the gel in a compressed state with some of the gel flowing into the recess provided in the cavity of the disposable portion.

In some implementations, the geometry of the reusable portion 100 and/or the disposable portion 200 can be configured to maximize coupling efficiency of the gel layer 260 when in the fully coupled state. For example, referring to FIG. 2A, the cavity 242 within the elongated housing 224 can have a recess 300 that surrounds at least part of a circumference of the distal optical member 130. The gel 260 flows into the recess 300 upon compression of the gel 260 when the connectors 120 and 220 are engaged with each other. FIG. 2A shows a recess 300 surrounding at least part of a circumference of the distal optical member 130. In FIG. 2A, which shows the uncompressed state of the gel 260, the gel is located only between the optical members 130 and 232, but the gel is not located within the recess 300. The distance D1, which is the thickness of the gel layer in the uncompressed state in FIG. 2A is about 1.5 mm. When the connectors 120 and 220 are engaged with each other, the gel layer 260 is compressed as shown in FIG. 2B, and a portion of the gel layer 260 is deformed and flows into the recess 300 to ensure that contact is maintained between the distal-most surface of the distal optical member 130 and gel 260. As shown in FIG. 2B, the distance D2 between facing surfaces of the optical member 232 and the distal optical member 130 is about 1 mm when the gel 260 is compressed.

As also shown in FIG. 2A, a centering ring 110 can be built into the reusable portion 100 to maintain the concentricity of the distal optical member 130 and the optical member 232 within the distal end of the disposable portion 200.

Figure 2C:
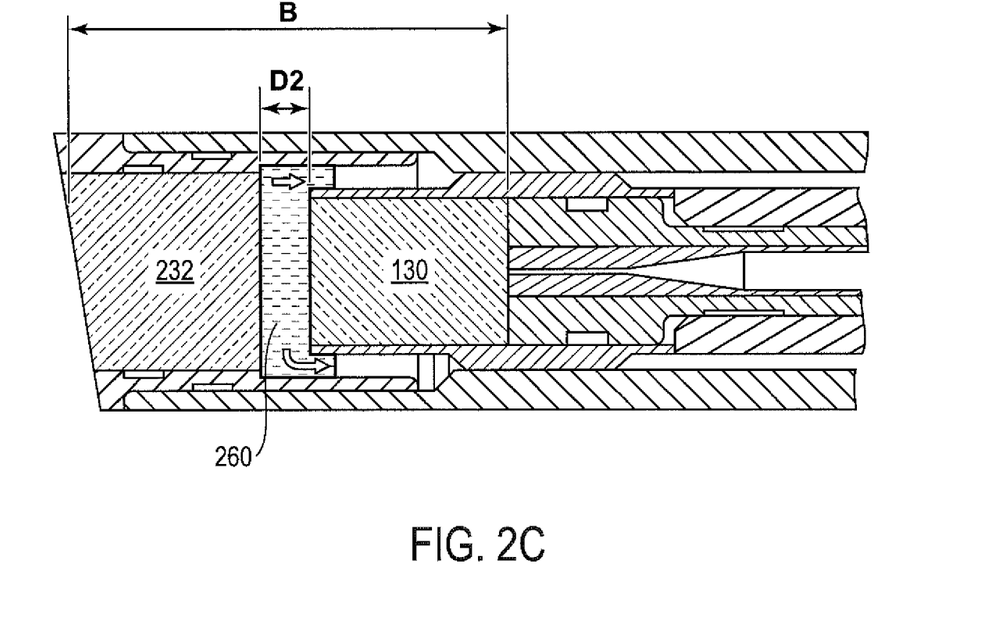
FIG. 2C is similar to FIG. 2B and shows some exemplary dimensions of the optical interface.

In the example of FIGS. 2A-2C, the diameter of the optical member 232 (dimension X in FIG. 2A) is 4 mm, and the diameter of the distal optical member 130 (dimension Y in FIG. 2A) is 3 mm. In the state in which the gel 260 is compressed to a thickness of 1 mm (dimension D2 in FIGS. 2B and 2C), FIG. 2C illustrates that there is minimal ill effects caused by the addition of the optical member 232 and gel 260 of the disposable portion 200 to the optical system of the reusable portion 100. In particular, the combined length of the optical member 232, the compressed gel 260 and the distal optical member 130 at the 3 mm diameter is 9 mm (dimension B in FIG. 2C).

Figure 3:
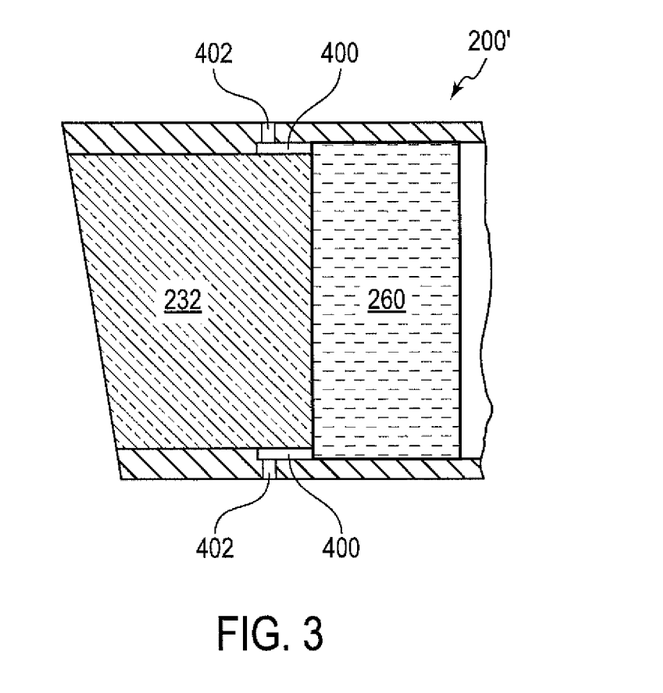
FIG. 3 shows a modified embodiment in which a recess is provided around the proximal end of the optical assembly of the disposable portion to receive some of the gel when the gel is compressed.

As shown in FIG. 3, the elongated housing 224 of a modified disposable portion 200' can include a recess 400 that surrounds at least part of a circumference of the proximal end of the optical member 232. The gel 260 flows into the recess 400 upon compression of the gel 260 when the connector 220 of the disposable insertion tip 200 is coupled to the connector 120 of the reusable portion 100 of the fiber optic probe. It is preferable to provide micro air holes 402 so that gas in the recess 400 can escape when the gel 260 is compressed and flows into the recess 400.

In one implementation, the distal optical member 130 and the optical member 232 can be comprised of BK7 optical glass. The outer material of the reusable portion 100 and of the disposable portion 200 can be comprised of Hytrel (7426 durometer with white colorant). Optical fibers within the reusable portion 100 may be designed as 50/60/70/160 um silica/silica/polyimide/acrylate. The fibers can be aligned with a custom glass fiber alignment ferrule manufactured by Accu-glass, fixtured in place with Epotek 353ND non-optical path epoxy, and flat polished at their end faces.

The fiber optic probe also can be configured by replacing the optical member 232 in the disposable portion 200 with a cap. In such an implementation, the cap is capable of transmitting light in a desired wavelength in a fashion similar to the optical member 232. The cap may be comprised of acrylic or glass, and may either be injection molded, cast, or produced in a similar means of high volume manufacturing. Thus, the cap would not induce undesired levels of birefringence due to the high volume manufacturing process. The distal optical member 130 also could be made of a plastic material such as acrylic.

Figure 4:
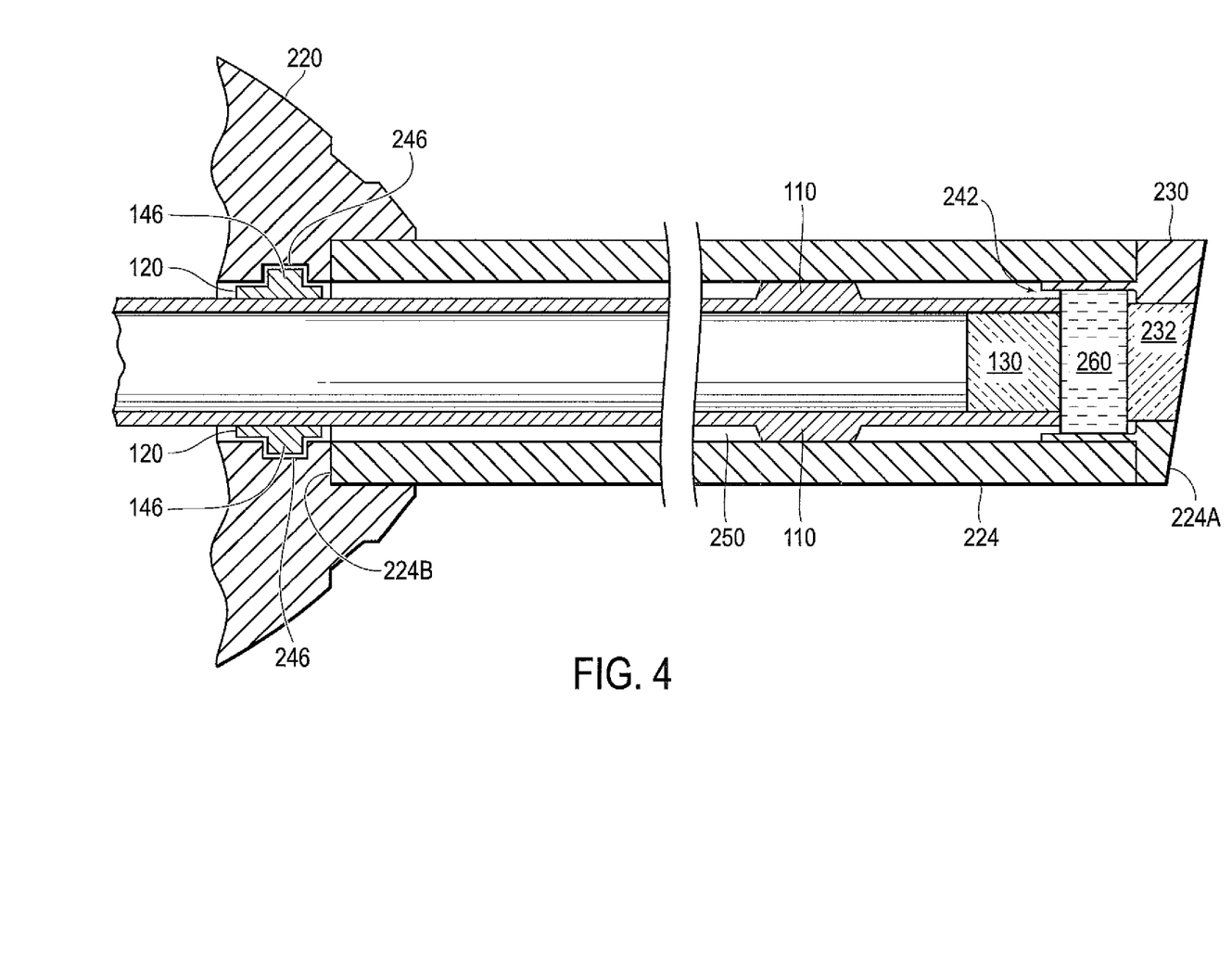
FIG. 4 shows a detailed partially cross-section view of a first type of connector structure between the reusable portion and the disposable portion.

FIG. 4 shows one embodiment of the connectors 120 and 220 of the reusable portion 100 and the disposable portion 200. In the FIG. 4 embodiment, the first coupling (on the disposable portion 200) is a plurality of recesses 246, and the second coupling (on the reusable portion 100) is a corresponding plurality of protrusions 146. The recesses 246 can be indentations or holes that receive the protrusions 146 of the second coupling. When the first coupling is engaged with the second coupling, the longitudinal and rotational positions of the connectors 120 and 220, and thus also of the distal optical member 130 and optical member 232 are fixed relative to each other. The first coupling and second coupling are positioned on the disposable portion 200 and the reusable portion 100, respectively, such that the gel 260 undergoes compression without undergoing plastic deformation when the first coupling and the second coupling are engaged with each other. This compression can ensure that the distal optical member 130 of the reusable portion 100 maintains contact with the gel layer 260. This compression can also provide for some ability of the gel 260 to conform to the distal optical member 130 in the reusable portion 100 in a case where the use of the device induces movement or shifting between the reusable portion 100 and the disposable portion 200. The gel layer 260 can undergo compression without plastic deformation, such as cracking and peeling, which may induce underside scattering or internal specular reflections in the optical path.

FIGS. 5A-5E show another embodiment of the connectors 120 and 220. In the embodiment of FIGS. 5A-5E, a biasing member such as a spring is included in one of the first and second couplings so as to more precisely control the force that is applied to the gel 260 when the gel is compressed between the distal optical member 130 and optical member 232. Such more precise control of the pressure ensures that adequate pressure is applied to the gel 260 to ensure good coupling without applying too much pressure to the gel 260, which could damage the gel 260 and thus adversely affect the optical coupling between the optical members 130 and 132.

Figure 5A:
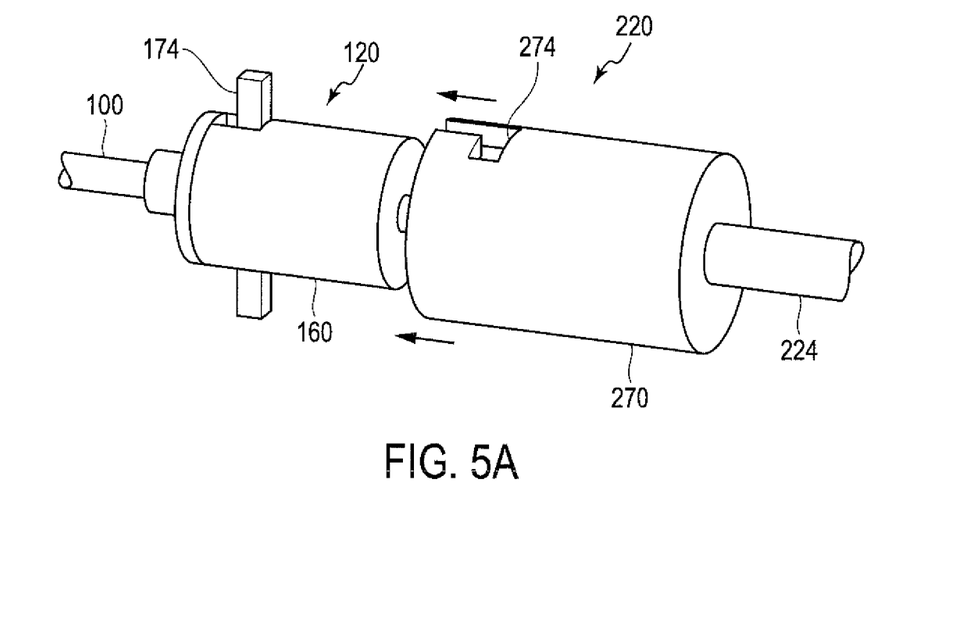
FIGS. 5A-5E show detailed views of a second type of connector structure between the reusable portion and the disposable portion.
Figure 5B:
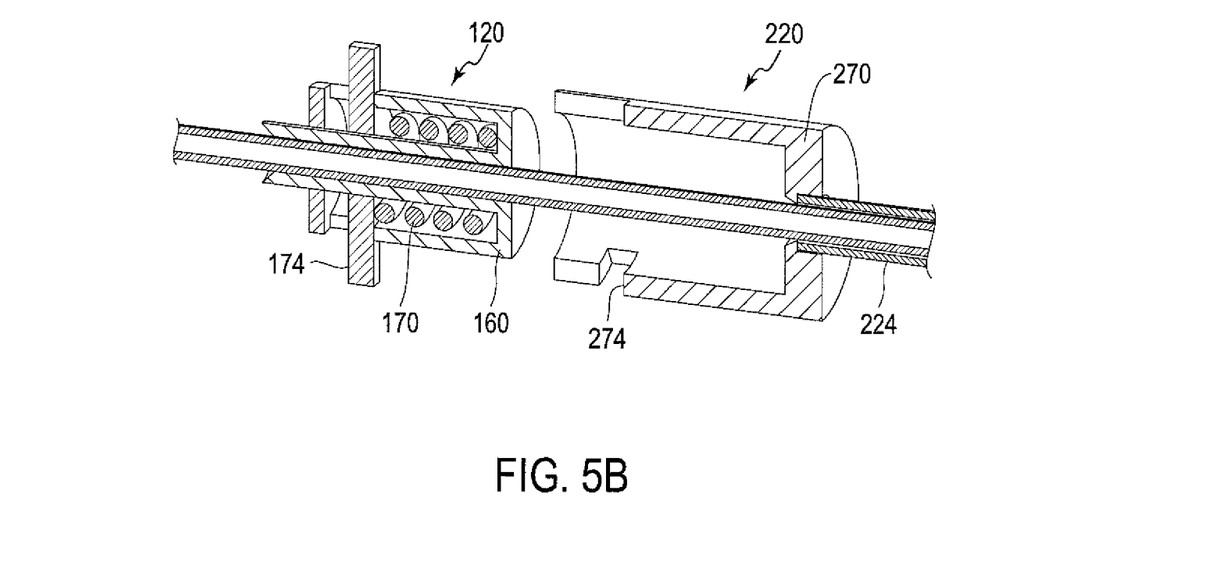
Figure 5C:
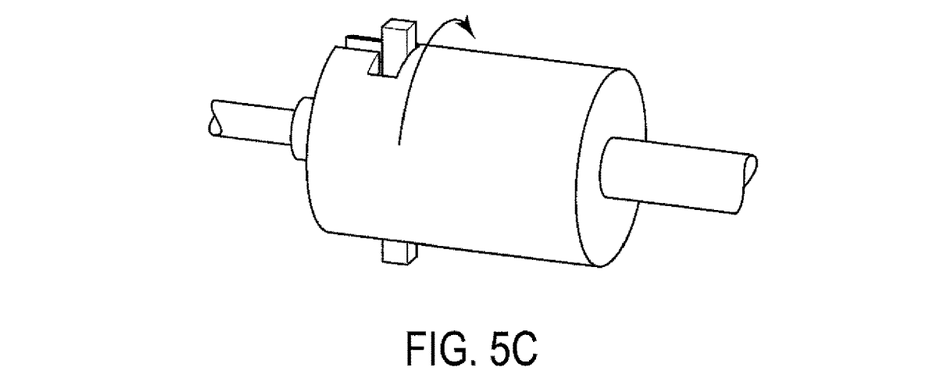
Figure 5D:
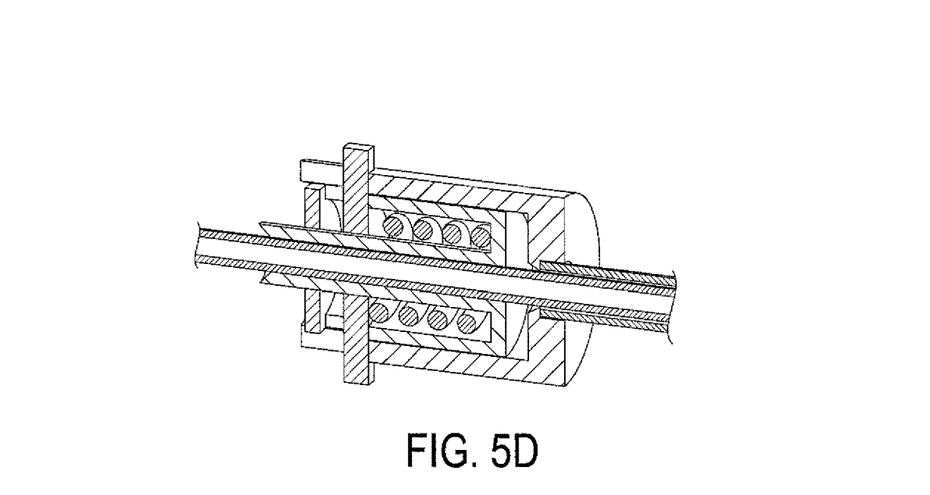
Figure 5E:
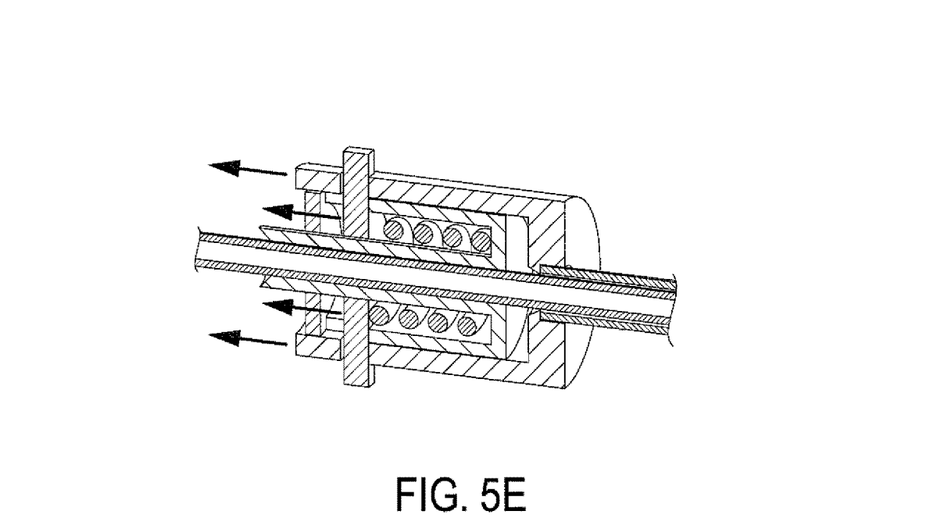

As shown in FIGS. 5A-5E, the connector 220 of the disposable portion 200 includes hollow first coupling 270, whereas the connector 120 of the reusable portion 100 includes a second coupling 160 that can be received by the first coupling 270 by moving the first and second couplings 270 and 160 relative to each other in the direction of the arrows in FIG. 5A. A stop or key 174 provided in the second coupling 160 slides into an L-shaped slot 274 provided in the first coupling 270, and then the disposable portion 200 is rotated relative to the reusable portion 100 in the direction of the arrow shown in FIG. 5C so that the stop 174 is captured by the circumferentially-extending leg of the L-shaped slot 274. The couplings 270 and 160 at that point are locked together. A spring 170 located inside of the second coupling 160 is biased between the stop 174 and an end wall of the second coupling 160. The spring 170 functions to limit the compression force applied to the gel 260 so that the gel compression force is equal to the tension force of the spring.

The illustrated exemplary embodiments of the fiber optic probe as set forth above are intended to be illustrative and not limiting. Various changes may be made without departing from the spirit and scope of the invention.

What is claimed is:

1. A disposable insertion tip of a low coherence enhanced backscattering (LEBS) fiber optic probe configured for characterization of tissue of a human subject; the disposable insertion tip comprising:

an elongated housing having a distal end and a proximal end, the distal end being insertable into a cavity of said human subject; an optical assembly disposed at the distal end of the elongated housing, the optical assembly including a proximal end that extends into a cavity provided within the elongated housing proximally of the distal end of the elongated housing;

wherein the cavity includes a recess that surrounds at least part of a circumference of the proximal end of the optical assembly, the gel flowing into the recess upon compression of the gel when the connector of the disposable insertion tip is coupled to the reusable portion of the fiber optic probe;

a connector disposed adjacent to the proximal end of the elongated housing, the connector including a first coupling that detachably couples to a mating, second coupling of a reusable portion of the LEBS fiber optic probe; and a pre-cured, compressible optically-transmissive gel disposed inside the cavity provided within the elongated housing and contacting at least the proximal end of the optical assembly such that there are no gaps between the proximal end of the optical assembly and the gel;

wherein the gel is positioned in an optical path of the disposable insertion tip;

wherein the gel is index-matched to an optical material of the optical assembly;

wherein the gel has a hardness of between about 60 shore 00 durometer and about 80 shore 00 durometer; and wherein said disposable insertion tip is configured to transmit light from said tissue of said subject to said reusable portion of the LEBS fiber optic probe.

2. The disposable insertion tip of claim 1, wherein the optical assembly is glass.

3. The disposable insertion tip of claim 1, wherein the optical assembly is a plastic material.

4. The disposable insertion tip of claim 1, wherein the gel has a hardness of about 77 shore 00 durometer.

5. The disposable insertion tip of claim 1, wherein the optical assembly is provided on a distal-most end of the elongated housing such that the optical assembly distally extends beyond the housing.

6. The disposable insertion tip of claim 1, wherein the pre-cured, compressible optically-transmissive gel disposed inside the cavity is for transfer of an optical signal.

7. A fiber optic probe comprising:

a disposable insertion tip of a low coherence enhanced backscattering (LEBS) fiber optic probe configured for characterization of tissue of a human subject; the disposable insertion tip comprising:

an elongated housing having a distal end and a proximal end, the distal end being insertable into a cavity of said human subject; an optical assembly disposed at the distal end of the elongated housing, the optical assembly including a proximal end that extends into a cavity provided within the elongated housing proximally of the distal end of the elongated housing;

a connector disposed adjacent to the proximal end of the elongated housing, the connector including a first coupling that detachably couples to a mating, second coupling of a reusable portion of the LEBS fiber optic probe;

a pre-cured, compressible optically-transmissive gel disposed inside the cavity provided within the elongated housing and contacting at least the proximal end of the optical assembly such that there are no gaps between the proximal end of the optical assembly and the gel;

wherein the gel is positioned in an optical path of the disposable insertion tip;

wherein the gel is index-matched to an optical material of the optical assembly;

wherein the gel has a hardness of between about 60 shore 00 durometer and about 80 shore 00 durometer;

wherein said disposable insertion tip is configured to transmit light from said tissue of said subject to said reusable portion of the LEBS fiber optic probe;

and a reusable portion having (i) a connector disposed proximally of a distal end of the reusable portion, the connector having the mating, second coupling that detachably couples to the first coupling of the disposable insertion tip, and (ii) an optical assembly including a distal optical member disposed at the distal end of the reusable portion and which is located distally of the second coupling, wherein when the first and second couplings are engaged with each other, the pre-cured, compressible optically-transmissive gel is compressed against and contacts at least a surface of the distal optical member of the reusable portion.

8. The fiber optic probe of claim 7, wherein the gel is index-matched to the optical assembly of the disposable insertion tip and to the distal optical member of the reusable portion.

9. The fiber optic probe of claim 7, wherein the cavity includes a recess that surrounds at least part of a circumference of the proximal end of the optical assembly of the disposable insertion tip, the gel flowing into the recess upon compression of the gel when the first and second couplings are engaged with each other.

10. The fiber optic probe of claim 9, wherein the cavity defines a second recess that surrounds at least part of a circumference of the distal optical member of the reusable portion, the gel flowing into the second recess upon compression of the gel when the first and second couplings are engaged with each other.

11. The fiber optic probe of claim 7, wherein the cavity defines a recess that surrounds at least part of a circumference of the distal optical member of the reusable portion, the gel flowing into the recess upon compression of the gel when the first and second couplings are engaged with each other.

12. The fiber optic probe of claim 7, wherein the distal optical member is glass.

13. The fiber optic probe of claim 7, wherein the distal optical member is a plastic material.

14. The fiber optic probe of claim 7, wherein the gel has a hardness of between about 60 shore 00 durometer and about 80 shore 00 durometer.

15. The fiber optic probe of claim 14, wherein the gel has a hardness of about 77 shore 00 durometer.

16. The fiber optic probe of claim 7, wherein the first and second couplings are positioned on the disposable insertion tip and the reusable portion, respectively, such that the gel undergoes compression without undergoing plastic deformation when the first and second couplings are engaged with each other.

17. The fiber optic probe of claim 7, wherein when the first and second couplings are engaged with each other, an optical path length from a distal end of the optical assembly of the disposable insertion tip to a proximal end of the distal optical member of the reusable portion is equal to a sum of:

(i) a length of the optical assembly of the disposable insertion tip, (ii) a compressed length of the pre-cured, compressible optically-transmissive gel, and (iii) a length of the distal optical member of the reusable portion.

* * * * *